US006060267A

United States Patent [19]
Hoshino et al.

[11] Patent Number: 6,060,267
[45] Date of Patent: May 9, 2000

[54] PRODUCTION OF VITAMIN $B_6$ WITH AN ENZYME-CONTAINING CELL EXTRACT

[75] Inventors: Tatsuo Hoshino, Kamakura; Masaaki Tazoe, Yokohama, both of Japan

[73] Assignee: Roche Vitamins, Inc., Parsippany, N.J.

[21] Appl. No.: 09/291,718

[22] Filed: Apr. 14, 1999

[30] Foreign Application Priority Data

Apr. 15, 1998 [EP]  European Pat. Off. .............. 98106812

[51] Int. Cl.$^7$ ............................. A23L 1/30; A61K 51/00; C12N 1/00; C12P 1/00; C12P 1/04
[52] U.S. Cl. ........................... 435/41; 426/311; 435/170; 435/183; 435/822
[58] Field of Search .............................. 435/41, 122, 170, 435/183, 822, 86; 424/1.73; 426/311; 514/52; 536/26.4

[56] References Cited

U.S. PATENT DOCUMENTS 5,766,894   6/1998   Hoshino et al. ......................... 435/122

FOREIGN PATENT DOCUMENTS 0 765 938 A2   4/1997   European Pat. Off. .

OTHER PUBLICATIONS

Yoshiki, T., et al., "Studies on Vitamin $B_6$ Metabolism in Microorganisms" *Agr. Biol. Chem.*, vol. 36, No. 2, pp. 189–197 (1972).

Scherr, G.H., et al., "The Directed Isolation of Mutants Producing Increased Amounts Of Metabolites" *J. Appl. Bact.* 25 (2), pp. 187–194 (1962).

Nishio, N., et al., Utilization of n–Paraffins and Vitamin $B_6$ Production by *Pichia guilliermondii* Wickerham, *Agr. Biol. Chem.*, 37(3), pp. 553–559, (1973).

Suzue, R., et al., "Biosynthesis of Vitamin $B_6$" *The Journal Of Vitaminology* 16, pp. 154–159, (1970).

Ishida, M., et al., "Studies on the Biosynthesis of Vitamin $B_6$" *Agr. Biol. Chem.*, vol. 34 No. 4, pp. 327–334 (1970).

Pflug, W., et al., "Vitamin $B_6$ Biosynthesis in *Bacillus Subtilis*" *Hoppe Seyler's Z. Physiol. Chem. Bd.* 359, 559–570 (1978).

Hill, R.E., et al., "The Biogenetic Anatomy of Vitamin $B_6$" *The Journal of Biological Chemistry* vol. 271, No. 48, pp. 30426–30435 (1996).

Hill, R.E., et al., "Biosynthesis of Vitamin $B_6$" in *Escherichia coli and Salmonella* 2nd ed., F.C. Neidhardt, Ed., pp. 695–703 (1996).

*Primary Examiner*—David M. Naff
*Assistant Examiner*—Deborah K. Ware
*Attorney, Agent, or Firm*—Mark E. Waddell; Stephen M. Haracz; Bryan Cave LLP

[57]  ABSTRACT

A process for the enzymatic production of vitamin $B_6$ which includes incubating 1-deoxy-D-threo-pentulose and 4-hydroxy-L-threonine with an enzyme system that is cell free or essentially cell free and prepared from the cells of a microorganism belonging to the genus Rhizobium, Sinorhizobium, Flavobacterium, Chryseobacterium, Lactobacillus, Arthrobacter, Bacillus, Klebsiella, Escherichia, Pseudomonas, Stenotrophomonas, Enterobacter, Serratia, Corynebacterium, Brevibacterium, Exiguobacterium, Saccharomyces, Yamadazyma, Pichia or Candida, in the presence of NADP$^+$, NAD$^+$, ATP. Manganese and magnesium ions stimulate the above reaction. This process affords high yields of vitamin $B_6$, a vitamin essential for the nutrition of animals, plants and microorganisms, and which is also useful as a medicine or food additive. In addition, an enzyme reaction system for producing vitamin $B_6$ and a process for making the enzyme reaction system are also provided.

22 Claims, No Drawings

PRODUCTION OF VITAMIN $B_6$ WITH AN ENZYME-CONTAINING CELL EXTRACT

FIELD OF THE INVENTION

This invention relates to a process for the enzymatic production of vitamin $B_6$ from 1-deoxy-D-threo-pentulose (referred to hereinafter as DTP) and 4-hydroxy-L-threonine (HT).

BACKGROUND OF THE INVENTION

There are many studies on the fermentative production of vitamin $B_6$. Various microorganisms belonging to the genera Saccharomyces [G. H. Scherr and M. E. Rafelson, J. Appl. Bacteriol. 25, 187–194 (1962)], Pichia [. Nishino, K. Fujii, and T. Kamikubo, Agric. Biol. Chem. 37, 553–559 (1973)], Klebsiella [R. Suzue and Y. Haruna, J. Vitaminol. 16, 154–159 (1970)], Achromobacter [M. Ishida and K. Shimura, Agric. Biol. Chem. 34, 327–334 (1970)], Bacillus [W. Pflug and F. Lingens, Hoppe-Seyler's Z. Physiol. Chem. 359, 559–570 (1978)] and Flavobacterium [Y. Tani, T. Nakamatsu, T. Izumi and K. Ogata, Agric. Biol. Chem. 36, 189–197 (1972)] are known to produce vitamin $B_6$. But no commercially attractive fermentation process for the production of vitamin $B_6$ has become known so far.

More recently, European Patent Publication 0 765 938 A2 describes a process for the fermentative production of vitamin $B_6$ by cultivating a microorganism belonging to the genus Rhizobium capable of producing the vitamin in a culture medium under aerobic conditions. The culture medium may contain, apart from assimilable carbon and digestible nitrogen sources, inorganic salts and other nutrients and further substances which improve the vitamin $B_6$ titer, such as DTP and HT. This process, however, is too inefficient.

SUMMARY OF THE INVENTION

Accordingly, it is an object of the present invention is to provide a highly efficient process for the enzymatic production of vitamin $B_6$ from DTP and HT.

The present invention is a process for the production of vitamin $B_6$ from 1-deoxy-D-threo-pentulose (DTP) and 4-hydroxy-L-threonine (HT). This process includes adding DTP and HT in the presence of nicotinamide adenine dinucleotide phosphate ($NADP^+$), nicotinamide adenine dinucleotide ($NAD^+$) and adenosine triphosphate (ATP) to an enzyme system prepared from cells of a microorganism which produce vitamin $B_6$ from DTP and HT.

Another embodiment is a process for producing vitamin $B_6$. This process includes: (a) adding DTP and HT to an enzyme system prepared from cells of a vitamin $B_6$-producing microorganism which produces vitamin $B_6$ from DTP and HT; (b) adding $NADP^+$, $NAD^+$ and ATP to the enzyme system; (c) initiating the enzyme reaction to produce vitamin $B_6$; and (d) recovering vitamin $B_6$ from the enzyme reaction system.

Another embodiment is an enzyme reaction system for producing vitamin $B_6$. This system includes: (a) substrates for the reaction system selected from DTP and HT; (b) an enzymatic system prepared from the cells of a microorganism which produces vitamin $B_6$ from DTP and HT; and (c) cofactors for the reaction system selected from $NADP^+$, $NAD^+$ and ATP.

Another embodiment is a process for producing an enzyme reaction system which produces vitamin $B_6$ from DTP and HT. This process includes (a) preparing an enzyme system from cells of a microorganism which produce vitamin $B_6$ from DTP and HT; (b) adding DTP and HT to the enzyme system; (b) adding $NADP^+$, $NAD^+$ and ATP to the enzyme system; and (c) allowing the enzyme system, DTP, HT, $NADP^+$, $NAD^+$ and ATP to react to produce vitamin $B_6$.

DETAILED DESCRIPTION OF THE INVENTION

The expression "vitamin $B_6$" as used in the present invention includes pyridoxol, pyridoxal and pyridoxamine. Vitamin $B_6$ is one of the essential vitamins for the nutrition of animals, plants and microorganisms, and is also very important as a medicine or food additive for humans.

The present invention makes it possible to produce vitamin $B_6$ from DTP and HT in higher efficiency than hitherto. In the present invention, it has been found that a cell-free extract prepared from the cells of a microorganism such as a microorganism of the genus Rhizobium, Sinorhizobium, Flavobacterium, Chryseobacterium, Lactobacillus, Arthrobacter, Bacillus, Klebsiella, Escherichia, Pseudomonas, Stenotrophomonas, Enterobacter, Serratia, Corynebacterium, Brevibacterium, Exiguobacterium, Saccharomyces, Yamadazyma, Pichia or Candida is capable of producing vitamin $B_6$ from DTP and HT in the presence of $NADP^+$, $NAD^+$ and ATP.

The present invention is thus a process for the enzymatic production of vitamin $B_6$ from DTP and HT which includes adding DTP and HT, in the presence of $NADP^+$, $NAD^+$ and ATP, to an enzyme system prepared from cells of a microorganism capable of producing vitamin $B_6$ from DTP and HT.

Another embodiment of the present invention is a process for the enzymatic production of vitamin $B_6$ which includes adding DTP and HT, in the presence of $NADP^+$, $NAD^+$ and ATP, to an enzyme reaction system containing a cell-free extract derived from a microorganism capable of producing vitamin $B_6$, such as one belonging to the genus Rhizobium, Sinorhizobium, Flavobacterium, Chryseobacterium, Lactobacillus, Arthrobacter, Bacillus, Klebsiella, Escherichia, Pseudomonas, Stenotrophomonas, Enterobacter, Serratia, Corynebacterium, Brevibacterium, Exiguobacterium, Saccharomyces, Yamadazyma, Pichia or Candida The content of vitamin $B_6$ in a reaction mixture can be determined by a bioassay with *Saccharomyces carlsbergensis* ATCC 9080 according to the method of D. R. Osborne and P. Voogt. [The Analysis of Nutrients in Foods, Academic Press, London, 224–227 (1978)] which is hereby incorporated by reference.

In the process according to the present invention, cells of a microorganism as described above are produced by cultivating the microorganism in a culture medium containing assimilable carbon sources, digestible nitrogen sources, inorganic salts and other nutrients necessary for the growth of the microorganism. In the present invention, the culture medium includes as the carbon source, for example, glucose, fructose, lactose, galactose, sucrose, maltose, starch, dextrin, glycerol and the like. The culture medium of the present invention includes as the nitrogen source, for example, peptone, yeast extract, soybean powder, corn steep liquor, meat extract, ammonium sulfate, ammonium nitrate, urea and mixtures thereof. Examples of the inorganic salts used in accordance with the present invention include sulfates, hydrochlorides and phosphates of calcium, magnesium, zinc, manganese, cobalt and iron. Optionally, conventional nutrient factors or an antifoaming agent, such as animal oil, vegetable oil or mineral oil, can also be included in the culture medium.

The pH of the culture medium may be from about 5 to about 9, preferably from about 6 to about 8. The temperature range for the cultivation of the microorganisms used in the present invention is suitably from about 10° C. to about 45° C., preferably from about 25° C. to about 40° C. The cultivation time of the microorganisms is normally from about 1 to about 5 days, preferably from about 1 to about 3 days. Aeration and agitation during the cultivation usually give favorable results.

The microorganisms which can be used in the process of the present invention include all the strains belonging to the genera Rhizobium, Sinorhizobium, Flavobacterium, Chryseobacterium, Lactobacillus, Arthrobacter, Bacillus, Klebsiella, Escherichia, Pseudomonas, Stenotrophomonas, Enterobacter, Serratia, Corynebacterium, Brevibacterium, Exiguobacterium, Saccharomyces, Yamadazyma, Pichia and Candida. Such microorganisms are available from public depositories (culture collection) to anyone upon request, such as the Institute of Fermentation, Osaka, Japan (IFO).

Examples of such deposited strains which can be used in accordance with the present invention include *Rhizobium meliloti* (also known as *Sinorhizobium meliloti*) IFO 14782 (DSM No. 10226), *Flavobacterium indologenes* (also known as *Chryseobacterium indologenes*) IFO 14944, *Lactobacillus brevis* IFO 13110, *Arthrobacter nicotianae* IFO 14234, *Bacillus subtilis* IFO 3007, *Klebsiella planticola* IFO 3317, *Escherichia coli* IFO 13168, *Pseudomonas putida* IFO 3738, *Stenotrophomonas maltophilia* (also known as *Pseudomonas maltophilia* or *Xanthomonas maltophilia*) IFO 12692, *Enterobacter cloacae* IFO 3320, *Serratia marcescens* IFO 12648, *Corynebacterium ammoniagenes* (also known as *Brevibacterium ammoniagenes*) IFO 12612, *Corynebacterium glutamicum* (also known as *Brevibacterium glutamicum*) IFO 12168, *Exiguobacterium acetylicum* (also known as *Brevibacterium acetylicum*) IFO 12146, *Pichia guilliermondii* (also known as *Yamadazyma guilliermondii*) IFO 10106, *Saccharomyces cerevisiae* IFO 0304 and IFO 0306 and *Candida tropicalis* IFO 0199 and IFO 0587. Among these microorganisms, the following are preferably used in the present invention: *Rhizobium meliloti* IFO 14782 (DSM No. 10226), *Flavobacterium indologenes* IFO 14944, *Bacillus subtilis* IFO 3007, *Escherichia coli* IFO 13168, *Serratia marcescens* IFO 12648, *Corynebacterium ammoniagenes* IFO 12612, *Corynebacterium glutamicum* IFO 12168, *Pichia guilliermondii* IFO 10106 and *Saccharomyces cerevisiae* IFO 0306. Other suitable microorganisms include *Stenotrophomonas maltophilia, Corynebacterium glutamicum, Exiguobacterium acetylicum*.

For preparation of a cell-free extract from the cells obtained by cultivation, general methods known in the art, such as, for example, sonication and cell breakage in the presence of glass beads or by a French press homogenizer, can be applied. If desired, treatment with a lytic enzyme, such as lysozyme or zymolase at 15° C. to 45° C., preferably at 20° C. to 40° C., for 1 to 3 hours can be also applied before the disruption of the cells in the above-mentioned way. For example, after centrifugation of the culture broth, the resulting cell pellet is washed with saline and suspended in a buffer such as Tris-HCl (pH 7.5) containing sucrose, dithiothreitol (DTT) and phenylmethylsulfonyl fluoride (PMSF) as general stabilizers of enzymes. After cell disruption, the resulting solution is centrifuged to separate the cell debris, and its supernatant is used as the cell-free extract.

The enzyme system of the present invention contains the cell-free extract as prepared above or those preparations partially purified by general methods for purification of enzymes, such as, for example, ammonium sulfate precipitation or gel filtration chromatography. Alternatively, the resting cells or the growing cells of the microorganism can also be used. Thus, as used herein, "prepared from" means that the enzyme system can either be a cell-free extract or a partially purified cell extract, so long as the preparation is able to make vitamin $B_6$ from DTP and HT as set forth herein.

In addition to the cell-free extract, DTP and HT are added to the enzyme system as substrates. In addition, $NADP^+$, $NAD^+$ and ATP are added to the enzyme system as cofactors. Thus, as used herein, the phrase, "enzyme reaction system" refers to the enzyme system, i.e., the cell-free extract or a partially purified cell extract, DTP, HT, $NADP^+$, $NAD^+$ and ATP. The amount of DTP, HT, $NADP^+$, $NAD^+$ and ATP to be added to the system can be varied depending on the reaction system employed. But, in general, the concentrations of DTP, HT, $NADP^+$, $NAD^+$ and ATP in the enzyme reaction system are 0.1 mM or more. Preferably, the concentration is from 1 mM to 10 mM for DTP and HT. Preferably, the concentration is from 0.05 mM to 5 mM, more preferably from 0.2 mM to 0.4 mM, for $NADP^+$ and $NAD^+$. Preferably, the concentration is from 1 mM to 20 mM, more preferably from 3 mM to 7 mM, for ATP.

The addition of manganese ions or magnesium ions to the enzyme reaction system of the present invention stimulates the reaction. The addition of both manganese and magnesium ions to the enzyme reaction system produces even higher yields of vitamin $B_6$ than addition of either type of ion alone. The present invention also includes in the enzyme reaction system salts giving rise to such ions; for example, the hydrochlorides, sulfates, nitrates or phosphates of manganese and magnesium can be employed. The amount of manganese ions and magnesium ions to be added can also be varied depending on the reaction system employed. In general, the concentration of manganese ions in the present enzyme reaction system ranges from 0.1 mM to 100 mM, preferably from 5 mM to 10 mM. In the case of magnesium ions, from 3 mM to 300 mM, preferably from 20 mM to 50 mM, are added to the present enzyme reaction system.

For initiating the enzyme reaction, a buffer solution which has no influence on vitamin $B_6$ production from DTP and HT can be used. Tris-HCl buffer is preferably used for this purpose.

The enzyme reaction is suitably effected at a pH range from 6.0 to 8.5, preferably in the range from 7.0 to 8.0. The reaction temperature for the enzyme reaction system is suitably from 15° C. to 45° C., preferably from 20° C. to 40° C. The incubation period for the enzymatic reaction of producing vitamin $B_6$ from DTP and HT may be varied depending on the reaction conditions, but is generally from 30 minutes to 5 hours, preferably from 2 hours to 4 hours.

Vitamin $B_6$ produced from DTP and HT under the conditions as described above can easily be recovered using a variety of methods. For example, after the reaction, proteins in the reaction mixture are precipitated by denaturation with heat, acid, alkali or organic solvent and removed by centrifugation. For this purpose a process generally used for extracting a certain product from the above supernatant may be employed which is applicable to the various properties of vitamin $B_6$. Thus, for example, vitamin $B_6$ in the supernatant is purified with an ion exchange resin. The desired product is further recrystallized from a mixture of alcohol and water.

The following examples are provided to further illustrate the processes of the present invention, as well as certain physical properties of the products produced therefrom. These examples are illustrative only and are not intended to limit the scope of the invention in any way.

EXAMPLES

Example 1

Preparation of cell-free extract

*Rhizobium meliloti* IFO 14782 (DSM No. 10226) was cultured in a seed medium containing 1% glucose, 0.5% polypeptone (Nippon Seiyaku Co., Japan), 0.2% yeast extract (Difco), 0.05% $MgSO_4.7H_2O$, 0.001% $MnSO_4.5H_2O$, and 0.001% $FeSO_4.7H_2O$ at 28° C. for 17 hours. The seed culture was transferred into a 500 ml flask containing 200 ml of a fermentation medium including 4% glucose, 2% polypeptone, 0.2% yeast extract, 0.05% $MgSO_4.7H_2O$, 0.05% $MnSO_4.5H_2O$, 0.001% $FeSO_4.7H_2O$, and one drop of antifoam CA-115 (Nippon Yushi Co., Japan). The flask was shaken on a flask shaker at 28° C. After cultivation for 72 hours, cells were harvested from 400 ml of the culture broth by centrifugation at 10,400×g for 10 minutes and washed twice with 0.85% NaCl solution and washed once with 10 mM Tris-HCl (pH 7.5) buffer containing 15% sucrose, 0.1 mM PMSF and 1 mM DTT and stored at −30° C. until use for preparation of the cell-free extract.

The following operations were all performed in ice water or at 4° C. The cells stored at −30° C. were thawed and suspended in 5 ml of 10 mM Tris-HCl (pH 7.5) buffer containing 15% sucrose, 0.1 mM PMSF and 1 mM DTT. The cell suspension was passed through a French press homogenizer (Ohtake Works Co,. Ltd.) at 200 kg/cm². The resulting homogenate was centrifuged at 34,800×g for 30 minutes to remove cell debris. Ten milliliters of the supernatant was dialyzed overnight against 1 liter of 80% ammonium sulfate solution containing 15% sucrose, 0.1 mM PMSF and 1 mM DTT. The precipitate was collected after centrifugation at 34,800×g for 30 minutes. The precipitate was dissolved in 10 milliliters of 10 mM Tris-HCl buffer (pH 7.5) containing 15% sucrose and 0.1 mM PMSF, then dialyzed overnight against the same buffer. The dialyzed solution was stored at −30° C. until use in the enzyme reaction. The protein content in the cell-free extract was determined by the Lowry method [Lowry et al., J. Biol. Chem. 193, 265 (1951)] to be 11.4 mg/ml.

Example 2

Enzymatic production of vitamin $B_6$ from DTP and HT

The enzyme reaction was carried out by incubating tubes containing 500 µl of the reaction mixture listed in Table 1 at 28° C. A complete reaction system contained 2.5 mM DTP, 2.5 mM HT, 0.38 mM $NADP^+$, 0.38 mM $NAD^+$, 5 mM ATP, 193.25 µl of the cell-free extract prepared in Example 1 and 80 mM Tris-HCl buffer, pH 7.50. After incubation for 2 hours, the reaction was stopped by heating in a boiling water bath for 3 minutes, centrifuged at 10,000×g for 10 minutes. Then, the supernatant was treated with phosphatase by incubating a tube containing 15 µl of the supernatant, 10 µl of 1 mg/ml acid phosphatase (Boehringer Mannheim GmbH, Germany) and 10 µl of 100 mM acetate buffer (pH 5.0) at 37° C. for 30 minutes. After incubation, 1,800 µl of water was added to the tube and determined by the microbiological method using *Saccharomyces carlsbergensis* ATCC 9080 as described below.

The standard solutions of pyridoxol (0–2 mg per milliliter) were diluted $1.21 \times 10^{-2}$ in distilled water. One hundred µl of the diluted standard solution or sample and 3 ml of the assay medium for vitamin $B_6$ (Nissui Co., Japan) containing *Saccharomyces carlsbergensis* ATCC 9080 were added to the tubes in this order and incubated with an angle of 30° at 28° C. After incubation for 17 hours, cell growth was stopped by adding 5 ml of 0.1 N hydrochloric acid to the tubes. Then the absorbance of the samples was measured at 660 nm.

The amount of vitamin $B_6$ in each sample was determined by comparing the turbidity of the sample with the standard growth curve of *Saccharomyces carlsbergensis* ATCC 9080. As a result of the process according to the present invention, 97 ng of vitamin $B_6$/ml/mg protein/hour were produced in the complete reaction system. On the other hand, no vitamin $B_6$ was produced in the reaction systems omitting one factor from the complete system. Furthermore, 119, 123 and 587 ng of vitamin $B_6$/ml/mg protein/hour were produced in the complete enzyme system supplemented with 8.4 mM $MnCl_2$, 32 mM $MgCl_2$ or both, respectively (Table 1).

The results indicate that the cell-free extract, $NADP^+$, $NAD^+$ and ATP are essential for vitamin $B_6$ production from DTP and HT. Moreover, $MnCl_2$, $MgCl_2$ and combinations thereof (especially) stimulate the production of vitamin $B_6$ in the present reaction system.

TABLE 1

Enzymatic production of vitamin $B_6$ from DTP and HT

| Reaction mixture | Produced vitamin $B_6$ (ng/ml/mg protein/hr) |
| --- | --- |
| Complete reaction system | 97 |
| Complete minus cell-free extract | 0 |
| Complete minus HT | 0 |
| Complete minus DTP | 0 |
| Complete minus $NADP^+$ | 0 |
| Complete minus $NAD^+$ | 0 |
| Complete minus ATP | 0 |
| Complete plus 8.4 mM $MnCl_2$ | 119 |
| Complete plus 32 mM $MgCl_2$ | 123 |
| Complete plus 8.4 mM $MnCl_2$ and 32 mM $MgCl_2$ | 587 |

Complete: 2.5 mM DTP, 2.5 mM HT, 0.38 mM $NADP^+$, 0.38 mM $NAD^+$, 5 mM ATP, 193.25 µl cell-free extract and 80 mM Tris-HCl buffer, pH 7.50

Example 3

Using the procedures of Examples 1 and 2, vitamin $B_6$ production using the cell-free extracts of various microorganisms was examined. Agar plates were inoculated with a loop full of cells from each strain listed in Table 2 (one strain per agar plate). The respective cells were cultured in the corresponding seed medium indicated in Table 2 at 28° C. for 17 hours. Two milliliters of each seed culture was transferred into a 500 ml flask containing 100 ml of the bulk medium and one drop of antifoam. Then, the flask was shaken on a flask shaker at 28° C. The compositions of seed and bulk media for cultivation of each strain listed on Table 2 are summarized in Table 3.

TABLE 2

Microorganisms and their cultivation media

| Microorganism | Media | |
| --- | --- | --- |
| | Seed | Bulk |
| *Flavobacterium indologenes* IFO 14944 | SM2 | FM2 |
| *Lactobacillus brevis* IFO 13110 | SM1 | FM1 |
| *Arthrobacter nicotianae* IFO 14234 | SM2 | FM2 |

TABLE 2-continued

Microorganisms and their cultivation media

| | Media | |
|---|---|---|
| Microorganism | Seed | Bulk |
| Bacillus subtilis IFO 3007 | SM2 | FM2 |
| Klebsiella planticola IFO 3317 | SM2 | FM2 |
| Escherichia coli IFO 13168 | SM2 | FM2 |
| Pseudomonas putida IFO 3738 | SM2 | FM2 |
| Stenotrophomonas maltophilia IFO 12692 | SM2 | FM2 |
| Enterobacter cloacae IFO 3320 | SM2 | FM2 |
| Serratia marcescens IFO 12648 | SM2 | FM2 |
| Corynebacterium ammoniagenes IFO 12612 | #802 | #802 |
| Corynebacterium glutamicum IFO 12168 | #802 | #802 |
| Exiguobacterium acetylicum IFO 12146 | #802 | #802 |
| Pichia guilliermondii IFO 10106 | ME | ME |
| Saccharomyces cerevisiae IFO 0304 | ME | ME |
| Saccharomyces cerevisiae IFO 0306 | ME | ME |
| Candida tropicalis IFO 0199 | ME | ME |
| Candida tropicalis IFO 0587 | ME | ME |

TABLE 3

Composition of the various media used in the present invention

| Ingredient | SM1 | SM2 | #802 | ME | FM1 | FM2 |
|---|---|---|---|---|---|---|
| Glucose | — | 1 | — | 1 | — | 2 |
| Peptone (Nippon Seiyaku) | 0.5 | 0.5 | 1.0 | 0.5 | 2 | 2 |
| Yeast extract (Difco) | 0.2 | 0.2 | 0.2 | 0.3 | 0.2 | 0.2 |
| Malt extract (Difco) | — | — | — | 0.3 | — | — |
| $MgSO_4 \cdot 7H_2O$ | 0.05 | 0.05 | 0.1 | | 0.05 | 0.05 |
| $MnSO_4 \cdot 5H_2O$ | 0.001 | 0.001 | — | | 0.05 | 0.05 |
| $FeSO_4 \cdot 7H_2O$ | 0.001 | 0.001 | — | | 0.001 | 0.001 |

After cultivation for 24 hours in the respective culture media, the cells of each strain were harvested from 400 ml of culture broth by centrifugation and washed twice with 0.85% NaCl solution and once with 10 mM Tris-HCl (pH 7.5) buffer containing 15% sucrose, 0.1 mM PMSF and 1 mM DTT. The resulting cells were suspended in 5 ml of the same buffer. Cells of *Flavobacterium indologenes* IFO 14944, *Lactobacillus brevis* IFO 13110, *Arthrobacter nicotianae* IFO 14234, *Bacillus subtilis* IFO 3007, *Klebsiella planticola* IFO 3317, *Escherichia coil* IFO 13168, *Pseudomonas putida* IFO 3738, *Stenotrophomonas maltophilia* IFO 12692, *Enterobacter cloacae* IFO 3320 or *Serratia marcescens* IFO 12648 were disrupted by passing through a French press homogenizer or by ultrasonic disintegration (Cosmo Bio Co., Ltd.). The other cell lines were treated with 2 mg lysozyme (Sigma) or 200 units zymolase (Sigma)/ml of cell suspension at 30° C. for 1 hour before the disruption as shown in Table 4. The resulting homogenate was centrifuged to remove cell debris and the supernatant was dialyzed against 10 mM Tris-HCl (pH 7.5) buffer containing 15% sucrose and 0.1 mM PMSF and used as the cell-free extract.

The enzyme reaction was carried out by incubating a tube with 500 μl of reaction mixture A that contains 2.5 mM DTP, 2.5 mM HT, 0.38 mM NADP+, 0.38 mM NAD+, 5 mM ATP, 193.25 μl cell-free extract and 80 mM Tris-HCl buffer, pH 7.50 or reaction mixture B that contains reaction mixture A supplemented with 8.4 mM $MnCl_2$ and 32 mM $MgCl_2$ at 28° C. After incubation for 2 hours, the reactions were stopped by heating in a boiling water bath for 3 minutes. Then, mixtures A and B were centrifuged at 10,000×g for 10 minutes and the supernatants were treated with acid phosphatase at 37° C. After incubation for 30 minutes, vitamin $B_6$ produced in each reaction mixture was determined by the bioassay method using *Saccharomyces carlsbergensis* ATCC 9080. As a result, ranges of 7–23 and 33–139 ng of vitamin $B_6$/ml/mg protein/hour were produced in the reaction mixtures A and B, respectively, as summarized in Table 4.

TABLE 4

Vitamin $B_6$ production by cell-free extract

| | | Vitamin $B_6$ (ng/ml/mg protein/hr.) | |
|---|---|---|---|
| Microorganism | Disruption method | Reaction mixture A | Reaction mixture B |
| Flavobacterium indologenes IFO 14944 | F | 23 | 139 |
| Lactobacillus brevis IFO 13110 | F | 7 | 37 |
| Arthrobacter nicotianae IFO 14234 | F | 19 | 100 |
| Bacillus subtilis IFO 3007 | F | 11 | 77 |
| Klebsiella planticola IFO 3317 | F | 13 | 76 |
| Escherichia coli IFO 13168 | F | 23 | 93 |
| Pseudomonas putida IFO 3738 | F | 7 | 33 |
| Stenotrophomonas maltophilia IFO 12692 | F | 9 | 49 |
| Enterobacter cloacae IFO 3320 | F | 8 | 35 |
| Serratia marcescens IFO 12648 | F | 13 | 69 |
| Corynebacterium ammoniagenes IFO 12612 | U* | 11 | 36 |
| Corynebacterium glutamicum IFO 12168 | U* | 12 | 42 |
| Exiguobacterium acetylicum IFO 12146 | U | 8 | 33 |
| Pichia guilliermondii IFO 10106 | U** | 16 | 53 |
| Saccharomyces cerevisiae IFO 0304 | U** | 8 | 28 |
| Saccharomyces cerevisiae IFO 0306 | U** | 13 | 44 |
| Candida tropicalis IFO 0199 | F** | 11 | 42 |
| Candida tropicalis IFO 0587 | F** | 10 | 43 |

F: French press, U: Ultrasonic disintegration
*Treatment with 2 mg lysozyme (Sigma)/ml of cell suspension at 30° C. for 1 hour before disruption.
**Treatment with 200 units zymolase (Sigma)/ml of cell suspension at 30° C. for 1 hour before disruption.
Reaction mixture A: 2.5 mM DTP, 2.5 mM HT, 0.38 mM NADP+, 0.38 mM NAD+, 5 mM ATP, cell-free extract and 80 mM Tris-HCl buffer, pH 7.50, in a total volume of 500 ml.
Reaction mixture B: 2.5 mM DTP, 2.5 mM HT, 0.38 mM NADP+, 0.38 mM NAD+, 5 mM ATP, 8.4 mM $MnCl_2$, 32 mM $MgCl_2$, cell-free extract and 80 mM Tris-HCl buffer, pH 7.50, in a total volume of 500 μl.

The invention being thus described, it will be obvious that the same may be viewed in many ways. Such variations are not to be regarded as a departure from the spirit and scope of the invention and all such modifications are intended to be included within the scope of the following claims.

What is claimed is:

1. A process for the production of vitamin $B_6$ from 1-deoxy-D-threo-pentulose (DTP) and 4-hydroxy-L-threonine (HT) comprising: (a) adding DTP and HT to an essentially cell-free enzyme system prepared from cells of a microorganism which produce vitamin $B_6$ from DTP and HT; (b) adding nicotinamide adenine dinucleotide phosphate (NADP+), nicotinamide adenine dinucleotide (NAD+) and adenosine triphosphate (ATP) to the enzyme system to form an enzyme reaction system; and (c) initiating an enzyme reaction in the enzyme reaction system to produce vitamin $B_6$.

2. A process according to claim 1 wherein DTP, HT, $NADP^+$, $NAD^+$ and ATP are present in the enzyme reaction system in a concentration of at least about 0.1 mM.

3. A process according to claim 1 wherein DTP and HT are present in the enzyme reaction system in a concentration from about 1 mM to about 10 mM.

4. A process according to claim 1 wherein $NADP^+$ and $NAD^+$ are present in the enzyme reaction system in a concentration from about 0.05 mM to about 5 mM.

5. A process according to claim 4 wherein $NADP^+$ and $NAD^+$ are present in the enzyme reaction system in a concentration from about 0.2 mM to about 4 mM.

6. A process according to claim 1 wherein ATP is present in the enzyme reaction system in a concentration from about 1 mM to about 20 mM.

7. A process according to claim 6 wherein ATP is present in the enzyme reaction system in a concentration from about 3 mM to about 7 mM.

8. A process according to claim 1 further comprising adding manganese ions, magnesium ions and mixtures thereof to the enzyme reaction system.

9. A process according to claim 8 wherein in the enzyme reaction system the concentration of manganese ions is from 0.1 mM to 100 mM and the concentration of magnesium ions is from 3 mM to 300 mM.

10. A process according to claim 9 wherein in the enzyme reaction system the concentration of manganese ions is from 5 mM to 10 mM and the concentration of magnesium ions is from 20 mM to 50 mM.

11. A process according to claim 1 wherein vitamin $B_6$ is produced by the enzyme reaction system at a pH range from 6.0 to 8.5, a temperature range from 15° C. to 45° C., for 30 minutes to 5 hours.

12. A process according to claim 11 wherein vitamin $B_6$ is produced by the enzyme reaction system at a pH range from 7.0 to 8.0, a temperature range from 20° C. to 40° C. for 2 to 4 hours.

13. A process according to claim 1 wherein the enzyme reaction system comprises a cell-free extract derived from a microorganism selected from the group consisting of Rhizobium, Sinorhizobium, Flavobacterium, Chryseobacterium, Lactobacillus, Arthrobacter, Bacillus, Klebsiella, Escherichia, Pseudomonas, Stenotrophomonas, Enterobacter, Serratia, Corynebacterium, Brevibacterium, Exiguobacterium, Saccharomyces, Yamadazyma, Pichia and Candida.

14. A process according to claim 13 wherein the enzyme reaction system comprises a cell-free extract derived from a microorganism selected from the group consisting of *Rhizobium meliloti, Flavobacterium indologenes, Lactobacillus brevis, Arthrobacter nicotianae, Bacillus subtilis, Klebsiella planticola, Escherichia coli, Pseudomonas putida, Stenotrophomonas maltophilia, Enterobacter cloacae, Serratia marcescens, Corynebacterium ammoniagenes, Corynebacterium glutamicum, Exiguobacterium acetylicum, Pichia guilliermondii, Saccharomyces cerevisiae, Candida tropicalis* and mixtures thereof.

15. A process according to claim 14, wherein the enzyme reaction system contains a cell-free extract derived from a microorganism selected from the group consisting of *Rhizobium meliloti, Flavobacterium indologenes, Bacillus subtilis, Escherichia coli, Serratia marcescens, Corynebacterium ammoniagenes, Corynebacterium glutamicum, Pichia guilliermondii, Saccharomyces cerevisiae* and mixtures thereof.

16. A process for producing vitamin $B_6$ comprising:
    (a) adding DTP and HT to an essentially cell-free enzyme system prepared from cells of a vitamin $B_6$-producing microorganism which produces vitamin $B_6$ from DTP and HT;
    (b) adding $NADP^+$, $NAD^+$ and ATP to the enzyme system to form an enzyme reaction system;
    (c) initiating an enzyme reaction in the enzyme reaction system to produce vitamin $B_6$; and
    (d) recovering vitamin $B_6$ from the enzyme reaction system.

17. An enzyme reaction system for producing vitamin $B_6$ comprising:
    (a) substrates selected from the group consisting of DTP and HT;
    (b) an essentially cell-free enzymatic system prepared from cells of a microorganism which produces vitamin $B_6$ from DTP and HT; and
    (c) cofactors selected from the group consisting of ($NADP^+$, $NAD^+$ and ATP).

18. An enzyme reaction system of claim 17 wherein the enzymatic system is cell-free.

19. An enzyme reaction system of claim 17 further comprising manganese ions, magnesium ions and mixtures thereof.

20. A process for producing an enzyme reaction system which produces vitamin $B_6$ from DTP and HT comprising:
    (a) preparing an essentially cell-free enzyme system from cells of a microorganism which produces vitamin $B_6$ from DTP and HT;
    (b) adding DTP and HT to the enzyme system; and
    (c) adding $NADP^+$, $NAD^+$ and ATP to the enzyme system.

21. A process for producing an enzyme reaction system according to claim 20 wherein the enzyme system is a cell-free extract.

22. A process for producing an enzyme reaction system according to claim 20 further comprising adding manganese ions, magnesium ions and mixtures thereof to the enzyme system.

* * * * *

UNITED STATES PATENT AND TRADEMARK OFFICE
CERTIFICATE OF CORRECTION

PATENT NO. : 6,060,267
DATED : May 9, 2000
INVENTOR(S) : Tatsuo HOSHINO, et al.

It is certified that error appears in the above-identified patent and that said Letters Patent is hereby corrected as shown below:

On the title page, under "[75] Inventors", in each of the cities of residence of the inventors, change "Kamakura" to --Kamakura-shi--, and "Yokohama" to --Yokohama-shi--.

Column 10, line 32, delete the "(" before NADP$^+$.

Signed and Sealed this

Twenty-seventh Day of February, 2001

Attest:

NICHOLAS P. GODICI

Attesting Officer

Acting Director of the United States Patent and Trademark Office